(12) United States Patent
Hassel et al.

(10) Patent No.: US 11,390,925 B2
(45) Date of Patent: Jul. 19, 2022

(54) METHOD FOR DETECTING A MICROORGANISM IN A SAMPLE

(71) Applicant: Corsham Science Limited, Corsham (GB)

(72) Inventors: Tamryn Jo Hassel, Corsham (GB); Ruth Catherine Massey, Corsley (GB); Leann Francis Bacon, Corsham (GB)

(73) Assignee: Corsham Science Limited, Corsham (GB)

( * ) Notice: Subject to any disclaimer, the term of this patent is extended or adjusted under 35 U.S.C. 154(b) by 103 days.

(21) Appl. No.: 16/637,462

(22) PCT Filed: Aug. 8, 2018

(86) PCT No.: PCT/EP2018/071463
§ 371 (c)(1),
(2) Date: Feb. 7, 2020

(87) PCT Pub. No.: WO2019/030261
PCT Pub. Date: Feb. 14, 2019

(65) Prior Publication Data
US 2020/0248238 A1 Aug. 6, 2020

(30) Foreign Application Priority Data

Aug. 8, 2017 (EP) .................................... 17185252

(51) Int. Cl.
| | | |
|---|---|---|
| *C12Q 1/689* | (2018.01) | |
| *C12N 1/06* | (2006.01) | |
| *C12Q 1/6806* | (2018.01) | |
| *C12Q 1/686* | (2018.01) | |

(52) U.S. Cl.
CPC ............ *C12Q 1/689* (2013.01); *C12N 1/066* (2013.01); *C12Q 1/6806* (2013.01); *C12Q 1/686* (2013.01)

(58) Field of Classification Search
CPC ...... C12Q 1/689; C12Q 1/6806; C12Q 1/686; C12N 1/066; C12N 1/06
See application file for complete search history.

(56) References Cited

U.S. PATENT DOCUMENTS

| | | | | |
|---|---|---|---|---|
| 2010/0273143 A1* | 10/2010 | Brewer | ................ | C12Q 1/6851 435/5 |
| 2012/0301907 A1* | 11/2012 | Sellappan | .............. | G01N 21/76 435/8 |
| 2017/0191114 A1* | 7/2017 | Kamba | ................ | G01N 1/4055 |

FOREIGN PATENT DOCUMENTS

| | | |
|---|---|---|
| EP | 0461477 A1 | 12/1991 |
| EP | 1593747 A1 | 11/2005 |
| WO | 9708293 A1 | 3/1997 |
| WO | 2009064766 A1 | 5/2009 |
| WO | 2012031156 A1 | 3/2012 |
| WO | 2017116694 A1 | 7/2017 |

OTHER PUBLICATIONS

International Search Report and Written Opinion for PCT/EP2018/0171463 dated Oct. 17, 2018, 16 pages.
Gonzalez J M et al, Multiple displacement amplification as a pre-polymerase chain reaction (pre-PCR) to process difficult to amplify samples and low copy number sequences from natural environments, Environmental Microbiology, Jan. 1, 2005, vol. 7, Nr.:7, pp. 1024-1028, Blackwell Science, GB.
Extended European Search Report for EP 17185252.8 dated Jan. 26, 2018, 10 pages.

* cited by examiner

*Primary Examiner* — Cynthia B Wilder
(74) *Attorney, Agent, or Firm* — Banner & Witcoff, Ltd.

(57) ABSTRACT

The present invention provides a method for detecting a microorganism in a sample, the method comprising: a) filtering a sample through a filter to entrap any microorganisms present in the sample; b) treating the filter to release genomic material or DNA from the entrapped microorganisms; c) amplifying the genomic material or DNA released from the entrapped microorganisms; and d) identifying specific regions of the genomic material or DNA to determine the presence, identify the species or quantify the approximate number of any entrapped microorganisms.

15 Claims, 1 Drawing Sheet
Specification includes a Sequence Listing.

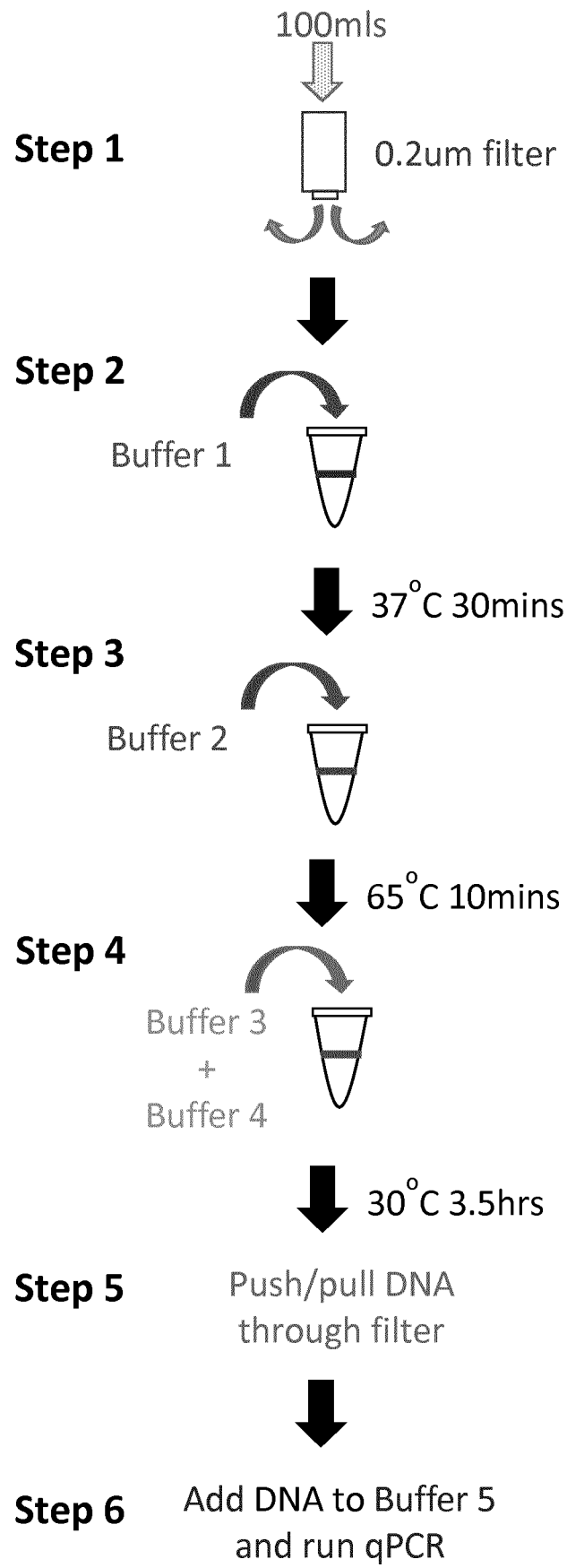

SEQUENCE LISTING

<160> NUMBER OF SEQ ID NOS: 10

<210> SEQ ID NO 1
<211> LENGTH: 100
<212> TYPE: DNA
<213> ORGANISM: Artificial Sequence
<220> FEATURE:
<223> OTHER INFORMATION: Positive control DNA sequence

<400> SEQUENCE: 1
gatcgctcag tcgcttttcg tactgcgcga aagttcgcac cgctcataca cttggttccg      60
aagcctgtcc tgatatatga atccaaacta gagcggggct                          100

<210> SEQ ID NO 2
<211> LENGTH: 19
<212> TYPE: DNA
<213> ORGANISM: Artificial Sequence
<220> FEATURE:

```
<223> OTHER INFORMATION: 16S Forward Primer

<400> SEQUENCE: 2
tcctacggga ggcagcagt                                                   19

<210> SEQ ID NO 3
<211> LENGTH: 26
<212> TYPE: DNA
<213> ORGANISM: Artificial Sequence
<220> FEATURE:
<223> OTHER INFORMATION: 16S Reverse Primer

<400> SEQUENCE: 3
ggactaccag ggtatctaat cctgtt                                           26

<210> SEQ ID NO 4
<211> LENGTH: 23
<212> TYPE: DNA
<213> ORGANISM: Artificial Sequence
<220> FEATURE:
<223> OTHER INFORMATION: 16S Probe

<400> SEQUENCE: 4
cgtattaccg cggctgctgg cac                                              23

<210> SEQ ID NO 5
<211> LENGTH: 20
<212> TYPE: DNA
<213> ORGANISM: Artificial Sequence
<220> FEATURE:
<223> OTHER INFORMATION: 18S Forward Primer

<400> SEQUENCE: 5
ctggcgatgg ttcattcaaa                                                  20

<210> SEQ ID NO 6
<211> LENGTH: 20
<212> TYPE: DNA
<213> ORGANISM: Artificial Sequence
<220> FEATURE:
<223> OTHER INFORMATION: 18S Reverse Primer

<400> SEQUENCE: 6
cttgccctcc aattgttcct                                                  20

<210> SEQ ID NO 7
<211> LENGTH: 19
<212> TYPE: DNA
<213> ORGANISM: Artificial Sequence
<220> FEATURE:
<223> OTHER INFORMATION: 18S Probe

<400> SEQUENCE: 7
taagggttcg attccggag                                                   19

<210> SEQ ID NO 8
<211> LENGTH: 22
<212> TYPE: DNA
<213> ORGANISM: Artificial Sequence
<220> FEATURE:
<223> OTHER INFORMATION: Positive control forward primer

<400> SEQUENCE: 8
gatcgctcag tcgcttttcg ta                                               22
```

```
<210> SEQ ID NO 9
<211> LENGTH: 22
<212> TYPE: DNA
<213> ORGANISM: Artificial Sequence
<220> FEATURE:
<223> OTHER INFORMATION: Positive control reverse primer

<400> SEQUENCE: 9
agccccgctc tagtttggat tc                                              22

<210> SEQ ID NO 10
<211> LENGTH: 26
<212> TYPE: DNA
<213> ORGANISM: Artificial Sequence
<220> FEATURE:
<223> OTHER INFORMATION: Positive control probe

<400> SEQUENCE: 10
tgcgcgaaag ttcgcaccgc tcatac                                          26
```

METHOD FOR DETECTING A MICROORGANISM IN A SAMPLE

This application incorporates by reference the contents of a 2.25 kb text file created on Feb. 4, 2020 and named "00048700199sequencelisting.txt," which is the sequence listing for this application.

BACKGROUND TO THE INVENTION

Within the pharmaceutical industry all products must be tested for sterility to ensure patient safety. The MHRA guidelines are that broth-based growth simulations are used to achieve this for sterility, simulation testing and validation testing. Prior to the distribution of a product into the market, nutrient rich broths such as tryptic soy broth (TSB) are used to determine the product's sterility. Such broths, when incubated at an appropriate temperature, provide suitable conditions for many microorganisms to grow. Microorganism growth in the broth therefore acts as an indicator of a contaminated product, and is assessed by a visual determination of the turbidity, or in some cases a colour change, of the broth after 14 days. By 14 days from sampling, the product can already be in the marketplace and sometimes even administered to a patient. Where broth turbidity is identified, an extensive investigation into its potential source is performed and often leads to recall and destruction of the product being tested.

The use of such broth-based tests is not limited to the pharmaceutical industry and applications can be found in, but are not limited to, the food, water and diagnostics industries.

While the premise behind the use of nutrient broth is logical, the present inventors have recognised the following limitations to its application, these being: 1) the test can take up to 14 days as some microorganisms are slow growing; 2) the identification of turbidity has a degree of subjectivity to it as it relies on the experience, skill and knowledge of the broth 'reader' to recognise turbidity within a solution; 3) due to the incubation time required for the test, contaminated products may have been administered to the patient before the contamination is detected, potentially leading to infection and death; and 4) not all microorganisms can grow in the recommended broths, resulting in potentially false negative results.

Following a recent incident where the limitations described above contributed to the death of three babies in the UK, the present inventors have developed an alternative test that overcomes the limitations of the current regulatory standard by providing a same-day determination of product contamination.

SUMMARY OF THE INVENTION

According to a first aspect the present invention provides a method for detecting a microorganism in a sample, the method comprising:

a) filtering a sample through a filter to entrap any microorganisms present in the sample;

b) treating the filter to release genomic material or DNA from the entrapped microorganisms;

c) amplifying the genomic material or DNA released from the entrapped microorganisms; and d) identifying specific regions of the genomic material or DNA to determine the presence, identify the species or quantify the approximate number of any entrapped microorganisms, wherein step c) is carried out on the filter.

Accordingly, the present invention provides DNA amplification technology capable of identifying the presence of individual microorganisms (such as single bacterial or fungal cells) within a matter of hours. The method of the present invention means that no culturing step is required. The rapid nature of DNA amplification allows users to obtain a result prior to product release onto the market, providing greater assurance at the point of release that the products released meet the stringent bioburden requirements of regulators.

Use of DNA amplification also greatly reduces subjectivity in the reading of a result. The presence or absence of DNA can be detected in different ways, many of which require minimal interpretation by the user. For example, using qPCR to interrogate for the presence of specific DNA sequences provides an easily distinguishable and machine readable fluorescence readout should the sequence be present. In particular, DNA analysis techniques give the same type of readout, irrespective of the source microorganisms. A user therefore only has to be trained for one type of readout. This is in contrast to the use of growth broths, where different microorganism cultures can grow to different extents and can have very different appearances. In some cases it can be very difficult to interpret what is happening in the broth.

The technique of the invention is not limited to only detecting microorganisms that are capable of growth in any given broth. DNA amplification can be carried out using robust and reproducible methods that work on any genomic material or DNA, irrespective of the microorganism that the genomic material or DNA is sourced from. This is particularly advantageous for detecting microorganisms that only multiply under very specific conditions, for example virus particles that require a suitable host cell to be present for particle replication.

By passing samples through a filter, any microorganisms present in the sample are entrapped on or in the filter. Suitable filters are typically used for sterilisation of the sample passing through the filter, and the filters are then typically discarded. The inventors have instead realised that the filter can form a key step in the process of detecting any microorganisms in the sample.

The inventors first exploit the fact that any microorganisms are entrapped by the small and easy to handle volume of the filter. Furthermore, the inventors have determined that it is possible to reproducibly apply the molecular biology techniques of genomic material or DNA release and amplification to any microorganisms in situ, i.e. on or in the filter. This avoids the need for any resuspension steps before further manipulation of the microorganisms. This minimises the number of steps conducted before the genomic material or DNA is amplified, minimising the risk of losing the microorganism, or losing the unamplified genomic material or DNA, and generating a false negative. This is particularly important as successful identification must be possible with low numbers of, and even single, microorganisms.

The method of the present invention can therefore allow a user to capture a single microorganism from a wide range of gaseous or liquid sample media, release and hold the microorganism's genomic material or DNA in or on the easily controllable and suitably sized volume of a filter, and exploit that control to subject the genomic material or DNA to amplification conditions in a robust and reproducible manner to provide a detectable signal in a short timeframe. The method may therefore be able to detect contamination levels as low as 1 colony forming unit (CFU) per 100 ml sample. In other words, the method may be able to detect contamination levels as low as one viable cell in any volume of sample.

Yet furthermore, should there be more than one type of microorganism, the genomic material or DNA from the different microorganisms should be amplified at similar rates. This is in contrast to the prior art method, where faster replicating microorganisms could out-compete slower replicating organisms. The present method therefore allows for the rapid and accurate detection of multiple contaminants i.e., indicating the presence of multiple types of microorganism. This overcomes a potential limitation of the prior art broth-based method where a fast-replicating but more benign microorganism could potentially mask the presence of a dangerous pathogen in a production facility.

The microorganism for detection can be one or more of a bacterium, a fungus, an archaea, a protozoan, an alga, a micro-animal or a virus. In particular, the microorganism can be selected from one or more of Gram positive bacteria, Gram negative bacteria, a yeast, a mould, a unicellular or diatom algae, or a DNA or RNA virus. As the method of the present invention releases and amplifies genomic material and/or DNA, the method can be applied with similar capability across a wide variety of microorganisms. This overcomes a significant prior art limitation where there is unlikely to be a single growth media suitable for all microorganisms that a user would ideally want to test for.

The method can be applied to a gaseous or liquid sample of at least about 0.01 µL. For example, a liquid sample may have a volume or at least about 500 µL, or a gaseous sample might have a volume of at least about 0.5 L. This allows for the method to be applied to a wide range of sample types, from small samples such as drops of urine up to large samples such as a few litres of saline solution from a saline production line.

The sample can be filtered through a filter having a pore size of about 0.01 µm to about 5 µm. Typically, the filter can have a pore size of about 0.2 µm. Pore sizes such as these should entrap all prokaryotic and eukaryotic cell types, as well as the majority of virus particles.

The genomic material or DNA can be released from the entrapped microorganisms by contacting the filter with sound energy, physical energy, or biological/chemical lysis such as an enzyme solution and/or a lysis buffer. As such, it is possible to release the genomic material or DNA from a wide variety of microorganisms.

The genomic material or DNA release method can employ sequential steps of breaking down cell walls of the microorganisms and lysing the microorganisms to release their genomic material or DNA. This allows for the release of genomic material or DNA from microorganisms that have more complex structures encapsulating the genomic material or DNA. This includes, for example, Gram-negative bacteria with multiple cell membranes or eukaryotes with cell and nucleus membranes.

The genomic material or DNA described herein may consist of all the genetic material contained in the contaminating microorganism. Typically the genomic material or DNA includes coding and/or non-coding DNA and/or RNA. In the event that the contaminating microorganism is a virus the genomic material or DNA may be just RNA.

The genomic material or DNA amplification can be done using a polymerase chain reaction (PCR) based amplification method, such as multiple displacement amplification (MDA). It is not necessary that amplification produces full-length genomic DNA strands. It is sufficient that shorter strands or fragments are produced, as long as the sum of those strands or fragments remains representative of the whole genome. MDA has benefits including a lower error frequency than standard PCR and can be performed in or on the filter without needing temperature cycling. A further advantage arises from the fact that the genomic material or DNA is represented by a large number of short strands or fragments. The short strands or fragments of DNA can be extracted or separated from the filter more readily and reliably.

After amplification of the genomic material or DNA, the amplified genomic material or DNA can be extracted or separated from the filter. This allows for the step of identifying specific regions of the genomic material or DNA to be carried out in an environment separate from the filter, for example, in a PCR device such as a qPCR device. After amplification of the genomic material or DNA, there is typically sufficient genomic material or DNA present that the control provided by having the DNA on the filter is no longer necessary.

Methods of extracting or separating amplified genomic material or DNA from the filter include using positive, negative or centrifugal force.

The identification of specific regions of the genomic material or DNA can be done using polymerase chain reaction (PCR) analysis. For example, quantitative PCR (qPCR) can be used. PCR analysis is rapid and reliable. The identification can be carried out on the filter or away from the filter after extracting or separating the amplified genomic material or DNA from the filter.

The sample can be a line flush, a bodily fluid sample (such as a blood or urine sample), a swab sample, a cough or air sample, a food substance, a solution for parenteral nutrition, a drink, a pharmaceutical composition or water.

According to a second aspect, the invention provides a method of diagnosing a disease or identifying a contaminant, the method comprising testing a sample obtained from a patient, animal or manufacturing process using the method of the first aspect of the invention.

BRIEF DESCRIPTION OF THE DRAWINGS

FIG. 1 provides a schematic flow chart outlining a method of the present invention. In step 1 a sample is filtered to trap any potentially contaminating microorganisms such as bacteria or fungi. In step 2 the cell walls of the trapped microorganisms are digested with enzymes in Buffer 1, then in step 3 the microorganisms are lysed using Buffer 2 to release their genomic material or DNA. In step 4 the genomic material or DNA is amplified in short sections of DNA using Buffer 3 and Buffer 4. These amplified sections are then separated from the filter in step 5. Finally, in step 6, specific regions of DNA are further amplified in Buffer 5 by qPCR to identify the presence of target microorganisms.

DESCRIPTION

The method of the present invention provides a method for detecting a microorganism in a sample, the method having multiple steps.

In step a), a sample is filtered through a filter to entrap any microorganisms present in the sample. Suitable filters are readily available commercially. For example, 'sterile filter units' are frequently used to sterilise liquids and gasses. To sterilise such a fluid, it is passed through the sterile filter into a sterile container. The sterile filter has a pore size that prevents passage of microorganisms, thus rendering the fluid that passes through sterile. The sterile filters are then generally discarded.

The microorganisms are entrapped by the filter. By this, we mean that during flow of the fluid through the filter, the microorganisms are entrapped by the filter such that the microorganisms do not end up in the filtrate. The precise mechanism by which the microorganisms are entrapped will depend on the type of filter employed. One option is that the microorganisms are entrapped within a matrix of filter material, for example, within a pore. Another option is that the microorganisms adhere to the surface of the filter, or are simply physically retained on the surface of the filter by the fluid flow. Typically the filter will only capture microorganisms in the form of whole cells. Any free-floating DNA that may be present in the sample will pass through the filter, i.e., it will not be entrapped. This reduces the risk of false positives that may result from pre-existing DNA that has not yet degraded within the initial sample.

The filtration step allows for the entrapment of one or more microorganisms from a wide range of fluid volumes. Suitable volumes for liquid samples include at least about 0.01 µL, or at least about 500 µL. Even when a single microorganism is present in a very large volume of fluid, by passing the whole volume through the filter, the single microorganism becomes entrapped by the filter. As such, the method of the invention can be applied to any large volumes, such as at least about 10 ml, preferably at least about 25 ml, more preferably at least about 50 ml.

In embodiments of the invention a liquid sample may have a volume of at least about 100 ml.

Suitable volumes for gaseous samples include at least about 0.01 µL, or at least about 0.5 L. Again, the method is particularly useful for identifying microorganisms in any large volumes of gas, such as at least about 10 L, preferably at least about 50 L, more preferably at least about 100 L.

The filtration step allows for the entrapment of microorganisms from a wide range of fluids. The samples for filtration can be liquids or gases. Some suitable fluids include: bodily fluids such as urine, saliva, blood, sputum or exhalation gases from the lungs; samples of fluid products taken from manufacturing processes; line flushes; waste streams; or liquid washes of products for distribution.

In embodiments of the invention wherein the sample is an exhalation gas, the volume of the sample may be at least about 0.5 L or in the range of about 0.5 L to about 10 L.

Typical filter pore sizes for entrapping microorganisms range from about 0.01 µm to about 5 µm. Preferably, the filter has a pore size of about 0.2 µm. Filters with such pore sizes are readily available commercially, particularly with 0.2 µm and 0.45 µm pore sizes.

In step b) the filter is treated to release genomic material or DNA from the entrapped microorganisms. The method of treatment is not particularly limited, other than by the fact that the genomic material or DNA must be released such that it can subsequently undergo amplification. Methods of releasing genomic DNA from various organism types are well known in the art.

Suitable methods of releasing genomic material or DNA from microorganisms include contacting the filter with sound energy, physical energy, or biological/chemical lysis such as an enzyme solution and/or a lysis buffer. One example of sound energy involves subjecting the microorganisms to ultrasonication. This is a commonly used cell disruption technique that releases the contents of a cell. Physical energy techniques for disrupting microorganisms are well known and include beadbeating or cryopulverisation, which can be particularly applicable to cells on the surface of a filter. Physical energy techniques that are particularly compatible with microorganisms entrapped within a filter pore include pressure cycling or nitrogen decompression.

Biological/Chemical lysis approaches to releasing genomic material or DNA from a microorganism, such as suitable enzyme solutions and lysis buffers, are well known and commercially available. For example, enzymes such as lysozyme are particularly effective for degrading microorganism cell walls. Lysis buffers comprising certain detergents (such as sodium dodecyl sulfate) can be particularly effective at dissolving microorganism cell walls.

The method of releasing genomic material or DNA can comprise sequential steps of breaking down cell walls of the microorganisms and lysing the microorganisms to release their genomic material or DNA. Certain microorganisms have multiple protective layers around their genomic material or DNA. For example, Gram-negative bacteria have multiple cell wall layers, and eukaryotic cells further shield their genomic DNA within a cell nucleus. Sequential steps of breaking down cell walls and further membranes can be employed to ensure that genomic material or DNA is released.

In step c) the genomic material or DNA is amplified. By this, we mean that the whole genome can be amplified, or that specific regions of interest of the genomic material or DNA can be amplified. Surprisingly, the present inventors have found that this amplification step can be carried out on the filter. Consequently, the released genomic material or DNA does not have to be separated from the filter before it is amplified, thereby avoiding the risk of DNA being lost during the separation process and improving both accuracy and sensitivity of the present method.

Amplification of the genomic material or DNA can be done by any of a number of well-known techniques, such as PCR based amplification methods. For example, some common techniques for whole genome amplification are degenerate oligonucleotide polymerase chain reaction (DOP-PCR), primer extension preamplification (PEP) and multiple displacement amplification (MDA). MDA is particularly preferred as it is less error prone, has reduced amplification bias and typically provides complete genome coverage.

The amplification enzymes can be denatured after sufficient amplification has been achieved.

In step d), specific regions of the genomic material or DNA are identified in order to determine the presence, identify the species or quantify the approximate number of microorganisms present in the sample. Methods of identifying specific sequences of DNA are known. For example, gene sequencing or PCR based methods such as qPCR can be used.

Essentially, the identification step merely has to confirm the presence or absence of genomic material or DNA. If genomic material or DNA is present, there has been contamination.

By 'specific regions' we therefore mean any specific regions that can be used to generically identify the presence of genomic material or DNA. In identifying the presence of genomic material or DNA, specific regions can be chosen that are common between microorganisms. For example, there are suitable 16S and 18S ribosomal regions that are conserved across bacterial and fungal cells. In addition, specific regions can be chosen that are specific to certain microorganisms. This allows for the additional capacity to specifically identify certain microorganisms. One advantage is that, alongside generically detecting the presence of mircoorganisms, a list of microorganisms of particular concern can be screened for just as rapidly. For example, identification of certain multidrug resistant bacteria, such as MRSA, may indicate an urgent need to go further than merely withholding batch release and initiate a wider decontamination of the production facility.

If required, specific regions of the genomic material or DNA can be further amplified. This can be done, for example, using PCR with primers directed only to those specific regions of genomic material or DNA. Where further amplification steps are used, it can be beneficial to denature any enzymes from the first amplification step before the further amplification step. This ensures that enzymes from the first amplification step do not interfere with the further amplification step.

With certain techniques, it would be possible to identify the specific regions of genomic material or DNA while still located on the filter. For example, DNA reporter dyes such as intercalator dyes could be applied to the filter. If DNA is present, the dye intercalates and becomes activated, confirming the presence of DNA.

In embodiments of the invention, there can be a further step ci) between step c) (amplification) and step d) (identification), wherein step ci) comprises extracting or separating the amplified genomic material or DNA from the filter. This allows for the specific regions of genomic material or DNA to be detected in an environment away from the filter. Owing to the fact that the genomic material or DNA has already been amplified in step c), there should be sufficient genomic material or DNA present that the loss of some genomic material or DNA on transfer no longer represents a significant risk of a false negative.

The amplified genomic material or DNA may be extracted or separated from the filter using positive, negative or centrifugal force. By this, we mean that the amplified genomic material or DNA can be extracted or separated from the filter either in the same direction as the original filtration or in the reverse direction to the original filtration. This can be done by pushing the amplified DNA through the filter (positive force) or drawing the amplified DNA through the filter (negative force), or using centrifugation to force the amplified DNA through the filter.

If the amplified genomic material or DNA is extracted or separated from the filter before identification, PCR based techniques such as qPCR can be used for the identification of specific regions of the genomic material or DNA. For example, qPCR can be used to provide more specific information than merely the presence or absence of DNA. For example, qPCR can be used to calculate how much contaminant was originally present. Furthermore, with the use of different reporter dyes, qPCR could be set up to identify different types or species of microorganism.

The method of the present invention was initially developed to replace the broth simulation and sterility test within the pharmaceutical sector. However, it also has utility in food and water industries, as well as clinical and veterinary infectious disease diagnostic settings.

The method of the invention can be used to test for any microorganism that is capable of having genomic material or DNA released in or on the filter. As mentioned, a wide variety of techniques are available for releasing genomic material or DNA from virtually all microorganisms. In theory, the method of the invention is therefore compatible with virtually all microorganisms. Such microorganisms include a bacterium, a fungus, an archaea, a protozoan, an alga, or a micro-animal. We also intend for the term 'microorganism' to cover virus particles. As such, the method of the present invention can also be used to test for a virus particle. The method of the invention could also be used to test for plant cells. More specifically, the method of the present invention can be used to test for Gram-positive bacteria, Gram-negative bacteria, a yeast, a mould, a unicellular or diatom algae.

The method of the invention can be applied to samples from a wide variety of sources. The sample can be a line flush. By this, we are referring to a manufacturing facility that transfers fluid products along lines. After the product has been transferred, the lines are flushed. The flush fluid can be used to determine if any microorganisms were left in the lines by a contaminated fluid. For example, in a pharmaceutical setting, the prior art method is that 100 ml of broth would be run through the tubing and over the apparatus used to prepare the pharmaceutical. In the present method, 100 ml of a washing solution can instead be run through the tubing and over the apparatus and then used as the sample of the invention.

The sample can be a bodily fluid, such as a blood or urine sample. Healthy urine contains no DNA-containing cells and can readily be analysed by the method of the invention. Healthy blood has DNA-containing cells, and would need to be subjected to a modified version of the method of the present invention to lyse blood cells prior to filtration.

The sample can be a swab sample. By this, we mean that the swab is washed using a carrier fluid, and the carrier fluid is the sample that is passed through the filter. The swab may be collected from any of a variety of sources, such as the surface of a product for release, from manufacturing equipment, or even from a human or animal body.

The sample can be an air sample. This could be the air within a controlled facility, such as a facility for the production and expansion of biopharmaceuticals. Air, and other gasses, can be passed directly through the filter without the need for a liquid to capture any microorganisms from the gas. This minimisation of the number of steps required before amplified DNA is present again minimises the chance of a false negative.

The method of the invention can be applied to environmental monitoring, such as in the microbiological or pharmaceutical environment. Conventionally, environmental monitoring is carried out by exposing agar plates to the environment, either by laying the agar plate open to the environment for a four hour period (passive air sampling), or by drawing air across the surface of the plate (active air sampling), or simply by contacting the agar plate with the surface to be investigated (a contact plate). Once the agar plates have been exposed to the environment they require incubation for at least three days. However, incubation periods of up to seven days may be needed. The method of present invention could be used to replace these traditional means of environmental monitoring. In this context the method of invention may be utilised with active air sampling to pull air across a filter, after which the treatment, amplification and identification steps may be carried out. Alternatively, a swab may be used to monitor a surface of interest, with the result swab being transferred to a solution, which can then be passed through a filter, after which the treatment, amplification and identification steps may be carried out. This application of the method of the invention would allow environmental monitoring results to be available before batches of a product leave a site, thereby providing greater quality assurance to the manufacturing process.

The sample can be a food substance, drink or pharmaceutical composition. These substances can be stored for prolonged periods of time and can contain suitable nutrients for microorganism growth. As these substances are intended for human or animal consumption, it is particularly important to ensure sterility of the substances leaving the production facility. This is particularly important for substances that are delivered intravenously, such as certain pharmaceutical compositions and with parenteral nutrition, as these bypass many of the human or animal body's defence mechanisms for invasive microorganisms.

The sample can be water. This can be drinking water, water intended for formulating various food, drink or pharmaceutical compositions for consumption, water intended for any compositions for long-term storage or industrial water. This could also be water used to wash lines, other manufacturing equipment or products for release.

As previously mentioned, the method of the present invention can be used on samples from the human or animal body. In particular, use of primers specific to different types of invasive microorganism allows for rapid diagnosis of the invading microorganism.

For example, the method can be used to rapidly detect the presence of invasive microorganisms in blood, and thus provide an early warning of sepsis. This would be particularly useful for immunocompromised patients where rapid medication is critical. The method of the invention can provide rapid identification of the specific microorganism, allowing for administration of an effective antimicrobial treatment rather than simply administering broad-spectrum antibiotics.

Furthermore, using primers specific to *Mycobacterium tuberculosis* could provide for a rapid convenient test for tuberculosis (TB) in humans and cattle. Currently, TB testing requires large pieces of equipment that require trucks for transportation to farms. The method of the present invention requires minimal equipment, and is amenable to a handheld device that can be battery operated. This allows for low cost and convenient TB testing devices.

EXAMPLES

Materials and Method

The following is described with reference to FIG. 1. To test for the presence of contaminating microorganisms in a volume of liquid of approximately 100 ml, it is first passed through a 0.2 µm filter which physically, through size exclusion, traps any bacterial or fungal cells (step 1). The cell walls of any microorganisms are digested by adding 1 µl Buffer 1 (an enzyme solution consisting of 1 mg/ml lysostaphin, 5 mg/ml lysozyme and 2.5 mg/ml glucanase) to the surface of the filter and incubating the filter at 37° C. for 30 mins (step 2). The genome of the microorganisms is released by lysing their cell membrane which is achieved by the addition of 1 µl of Buffer 2 (200 mM KOH, 50 mM DTT) to the surface of the filter and incubation at 65° C. for 10 mins (step 3), followed by addition of 1 µl of Buffer 3 (900 mM Tris HCl, 300 mM KCl, 200 mM HCl) to the surface of the filter. The released genome is amplified (replicated/copied) in random sections using a multiple displacement amplification (MDA) method such as that described here: adding 9 µl Buffer 4 (0.45 µl Phi29 enzyme, 0.09 µl BSA, 0.9 µl Phi29 Buffer, 0.45 µl Random hexamers (20 µM), 0.45 µl dNTPs (40 µM) 6.5 µl water) to the surface of the filter and incubating the filter at 30° C. for 3 hrs. The enzymes are denatured to prevent them from interfering with the next amplification step by incubation at 65° C. for 10 mins (step 4). The amplified sections of DNA are extracted through the filter (by positive, negative or centrifugal force) (step 5).

Aliquots of 2 µl of the amplified DNA are added to Buffer 5 (10 µl Taqman probe, 4 µl mixed primers (10 uM), 0.05 µl FAM TAMRA probe) containing primers and fluorescent probes specific to the conserved region in the 16S and 18S ribosomal regions present in bacterial and fungal cells listed below in table 1 (step 6). The reaction is placed in a StepOne Plus qPCR machine, on the following program:

| | |
|---|---|
| 95° C. 10 mins | |
| 95° C. 15 secs | |
| 60° C. 1 min | } 40 cycles |

Positive Control.

To ensure the qPCR section of the test is functional and does not produce false negative results, a positive control has been developed for the test. We incorporate a 100 bp strand of synthesised DNA, the sequence of which was randomly generated and tested by a NCBI BLAST search to ensure it is not found in any known bacterial or fungal species. Primers were designed for this sequence and a probe with the fluorescent tag JOE to distinguish from the fluorescent probe FAM used for bacterial and fungal strains (Table 1).

Positive control DNA sequence:

(SEQ ID NO: 1)
GATCGCTCAGTCGCTTTTCGTACTGCGCGAAAGTTCGCACCGCTCATACA
CTTGGTTCCGAAGCCTGTCCTGATATATGAATCCAAACTAGAGCGGGGCT

Negative Control.

Ultra-pure sterile water is used to represent a 'no template' or negative control for all experiments. The CT value this provides in the qPCR reaction is also used as the base-line to determine a positive reaction in the samples, i.e. for a sample to be considered positive it needs to have a CT value lower than the CT values for this control by at least one unit.

TABLE 1

| Primer/Probe | Sequence |
|---|---|
| 16S Forward | TCC TAC GGG AGG CAG CAG T<br>(SEQ ID NO: 2) |
| 16S Reverse | GGA CTA CCA GGG TAT CTA ATC CTG TT<br>(SEQ ID NO: 3) |
| 16S Probe | FAM-CGT ATT ACC GGG GCT GCT GGG AC-TAMRA<br>(SEQ ID NO: 4) |
| 18S Forward | CTG GGG ATG GTT CAT TCA AA<br>(SEQ ID NO: 5) |
| 18S Reverse | CTT GCC CTC CAA TTG TTC CT<br>(SEQ ID NO: 6) |
| 18S Probe | FAM TAA GGG TTC GAT TCC GGA G TAMRA<br>(SEQ ID NO: 7) |
| Positive Control Forward Primer | GATCGCTCAGTCGCTTTTCGTA<br>(SEQ ID NO: 8) |
| Positive Control Reverse Primer | AGCCCCGCTCTAGTTTGGATTC<br>(SEQ ID NO: 9) |

TABLE 1-continued

| Primer/Probe | Sequence |
|---|---|
| Positive Control Probe | JOE TGCGCGAAAGTTCGCACCGCTCATAC BHQ1 (SEQ ID NO: 10) |

Results

To ensure our test works on all of the pharmacopoeial microorganisms, including *Staphylococcus aureus*, *Bacillus subtilis*, *Pseudomonas aeruginosa*, *Micrococcus luteus*, *Candida albicans* and *Aspergillus brasiliensis*, we spiked test solutions of water with between 1 and 100 colony forming units (CFU) of each organism. Each was grown in Tryptic Soy Broth (TSB) overnight (at 37° C. for *S. aureus*, *B. subtilis* and *P. aeruginosa* and 30° C. for *M. luteus*, *A. brasiliensis* and *C. albicans*). The following day cultures were diluted to an appropriate volume and an aliquot was either plated to accurately determine the cell density or put through the test. The results in table 2 show the test was effective in detecting these organisms.

TABLE 2

| | Experiment 1 | | Experiment 2 | | Experiment 3 | |
|---|---|---|---|---|---|---|
| Sample | CFU | CT | CFU | CT | CFU | CT |
| S. aureus | 19 | 31.975 | 21 | 32.966 | 15 | 33.146 |
| B. subtilis | 8 | 33.185 | 9 | 31.887 | 5 | 32.636 |
| P. aeruginosa | 7 | 32.433 | 5 | 32.39 | 8 | 33.578 |
| M. luteus | 16 | 32.323 | 11 | 32.017 | 4 | 31.836 |
| C. albicans | 3 | 33.001 | 5 | 28.013 | 2 | 31.38 |
| A. Brasiliensis | 9 | 32.122 | 9 | 32.122 | 8 | 32.147 |
| Control | | 34.085 | | 33.977 | | 34.309 |

Following the development of the test on the six pharmacopoeial micro-organisms, it was performed on four extra bacterial species to determine its broad applicability. Water was spiked with 1 to 100 colony forming units of *Staphylococcus epidermidis*, *Salmonella* Dublin, *Escherichia coli* or *Lactobacillus lactis*, and the test performed as described above. The results in Table 3 show the test is effective in detecting these species.

TABLE 3

| Bacteria Species | Replicate number | No. of cells (CFU) | CT |
|---|---|---|---|
| Staphylococcus epidermidis | 1 | 41 | 31.713 |
| | 2 | 15 | 32.049 |
| | 3 | 17 | 31.987 |
| Salmonella dublin | 1 | 22 | 32.024 |
| | 2 | 18 | 31.5 |
| | 3 | 17 | 31.554 |
| | 4 | 7 | 31.711 |
| Escherichia coli | 1 | 21 | 31.566 |
| | 2 | 20 | 31.471 |
| | 3 | 14 | 31.824 |
| | 4 | 15 | 31.983 |
| Lactobacillus lactis | 1 | 17 | 31.617 |
| | 2 | 18 | 31.872 |
| | 3 | 23 | 30.7 |
| | 4 | 14 | 31.244 |
| Control | 1 | NA | 33.457 |
| Control | 2 | NA | 33.975 |

To test the effectivity of the positive control, qPCR reactions were prepared as described above with the 18S, 16S, including the positive control primers along with all associated probes. For each reaction *Bacillus subtilis* genomic DNA and the positive control DNA were used as templates either mixed together or separately to check the specificity of the primers. Table 4 shows that the primers and probes do not display any non-specific amplification.

TABLE 4

| Sample | Probe | CT | Repeat CT |
|---|---|---|---|
| B. subtilis and positive DNA mixed | 18S and 16S | 16.47 | 16.35 |
| | Positive | 19.97 | 19.87 |
| B. subtilis DNA only | 18S and 16S | 15.74 | 15.48 |
| | Positive | 35.17 | 35.71 |
| Positive DNA only | 18S and 16S | No signal | No signal |
| | Positive | 19.52 | 19.3 |

The results indicate a significant improvement in sensitivity compared to a conventional broth test, for which a sensitivity of 10,000 CFU in a 100 ml sample is generally accepted. In contrast the method of the present invention can potentially detect just one CFU in a 100 ml sample. Additionally, results were obtained in just one day, compared to up to 14 days for a conventional broth test.

The invention claimed is:

1. A method for detecting a microorganism in a sample, the method comprising:
   a) filtering a sample through a filter to entrap on or in the filter any microorganisms present in the sample;
   b) treating the filter to release genomic material or DNA from the entrapped microorganisms on or in the filter;
   c) amplifying the genomic material or DNA released from the entrapped microorganisms, wherein amplification comprises multiple displacement amplification and wherein the amplification is carried out on or in the filter; and
   d) identifying specific regions of the genomic material or DNA to determine the presence, identify the species or quantify the approximate number of any entrapped microorganisms.

2. The method of claim 1, wherein the microorganism is a bacterium, a fungus, an archaeon, a protozoan, an alga, a micro-animal or a virus.

3. The method of claim 1, wherein the microorganism is selected from one or more of Gram positive bacteria, Gram negative bacteria, yeast, mould, unicellular or diatom algae, or is a DNA or RNA virus.

4. The method of claim 1, wherein step a) comprises filtering the sample through a filter having a pore size of about 0.01 μm to about 5 μm.

5. The method of claim 4, wherein the filter has a pore size of about 0.2 μm.

6. The method of claim 1, wherein step b) comprises contacting the filter with sound energy, physical energy, or chemical lysis.

7. The method of claim 1, wherein step b) comprises sequential steps of breaking down cell walls of the one or more microorganisms and lysing the entrapped microorganisms to release their genomic material or DNA on or in the filter.

8. The method of claim 1, further comprising step ci) between step c) and step d), step ci) comprising extracting genomic material or DNA from the filter.

9. The method of claim 8, wherein step ci) comprises extracting genomic material or DNA from the filter using positive, negative or centrifugal force.

10. The method of claim 1, wherein step d) comprises identifying specific regions of the genomic material or DNA using polymerase chain reaction (PCR).

11. The method of claim 10, wherein step d) comprises quantitative polymerase chain reaction (qPCR).

12. The method of claim 1, wherein the sample is a line flush, a bodily fluid sample, a swab sample, a cough or air sample, a food substance, a solution for parenteral nutrition, a drink, a pharmaceutical composition or water.

13. A method of diagnosing a disease caused by an invasive microorganism, the method comprising testing a sample obtained from a patient or animal according to the method of claim 1, wherein the presence of the invasive microorganism indicates a positive diagnosis of the disease.

14. The method of claim 6, wherein step b) comprises chemical lysis, wherein the chemical lysis comprises an enzyme solution and/or a lysis buffer.

15. The method of claim 12, wherein the sample is a bodily fluid sample, wherein the bodily fluid sample is a blood or a urine sample.

* * * * *